US012558368B2

(12) United States Patent
Von Borstel et al.

(10) Patent No.: US 12,558,368 B2
(45) Date of Patent: Feb. 24, 2026

(54) COMPOSITIONS AND DEVICES FOR SYSTEMIC DELIVERY OF URIDINE

(71) Applicant: PHARMA CINQ, LLC, Rockville, MD (US)

(72) Inventors: Reid W. Von Borstel, Potomac, MD (US); Rolando Alejandro Garcia Garcia, Germantown, MD (US)

(73) Assignee: PHARMA CINQ, LLC, Rockville, MD (US)

( * ) Notice: Subject to any disclaimer, the term of this patent is extended or adjusted under 35 U.S.C. 154(b) by 1352 days.

(21) Appl. No.: 16/961,711

(22) PCT Filed: Feb. 1, 2019

(86) PCT No.: PCT/US2019/016246
§ 371 (c)(1),
(2) Date: Jul. 13, 2020

(87) PCT Pub. No.: WO2019/152776
PCT Pub. Date: Aug. 8, 2019

(65) Prior Publication Data
US 2021/0187001 A1 Jun. 24, 2021

Related U.S. Application Data

(60) Provisional application No. 62/715,848, filed on Aug. 8, 2018, provisional application No. 62/624,911, filed on Feb. 1, 2018.

(51) Int. Cl.
| | |
|---|---|
| *A61K 31/7072* | (2006.01) |
| *A61K 9/00* | (2006.01) |
| *A61K 31/19* | (2006.01) |
| *A61K 33/00* | (2006.01) |
| *A61K 33/06* | (2006.01) |
| *A61M 5/14* | (2006.01) |
| *A61M 5/162* | (2006.01) |
| *A61P 43/00* | (2006.01) |

(52) U.S. Cl.
CPC ........ *A61K 31/7072* (2013.01); *A61K 9/0019* (2013.01); *A61K 31/19* (2013.01); *A61K 33/00* (2013.01); *A61K 33/06* (2013.01); *A61M 5/14* (2013.01); *A61M 5/162* (2013.01); *A61P 43/00* (2018.01)

(58) Field of Classification Search
CPC .............. A61K 31/7072; A61K 9/0019; A61K 31/19; A61K 33/00; A61K 33/06; A61K 9/0021; A61K 31/192; A61K 45/06; A61K 2300/00; A61M 5/14; A61M 5/162; A61P 43/00; A61P 25/00
See application file for complete search history.

(56) References Cited

U.S. PATENT DOCUMENTS

| | | | |
|---|---|---|---|
| 4,663,289 A | | 5/1987 | Veech |
| 5,654,266 A | * | 8/1997 | Chen .................... A01N 1/0226 |
| | | | 514/546 |
| 5,858,005 A | | 1/1999 | Kriesel |
| 5,876,757 A | | 3/1999 | McCarty |
| 6,344,447 B2 | | 2/2002 | von Borstel et al. |
| 6,956,028 B2 | | 10/2005 | von Borstel |
| 6,989,376 B2 | | 1/2006 | Watkins et al. |
| 7,709,459 B2 | | 5/2010 | von Borstel et al. |
| 9,555,077 B2 | | 1/2017 | Murakami et al. |
| 2004/0068015 A1 | | 4/2004 | Matsuno et al. |
| 2015/0297622 A1 | | 10/2015 | Groenendijk et al. |
| 2016/0354332 A1 | | 12/2016 | Sabatini et al. |
| 2017/0100354 A1 | | 4/2017 | Bjornsson et al. |
| 2017/0209476 A1 | | 7/2017 | von Borstel |
| 2017/0266148 A1 | | 9/2017 | D'Agostino et al. |
| 2017/0290792 A1 | | 10/2017 | Cavaleri |

FOREIGN PATENT DOCUMENTS

| | | |
|---|---|---|
| EP | 1109453 B1 | 7/2012 |
| JP | H10-995730 A | 4/1998 |
| JP | 2008-513453 A | 5/2008 |
| JP | 2013-064026 A | 4/2013 |
| KR | 10-2009-0079714 A | 1/2008 |
| WO | 2017184788 A1 | 10/2017 |
| WO | 2018038609 A1 | 3/2018 |
| WO | 2018187852 A1 | 10/2018 |

OTHER PUBLICATIONS

Kim et al. Biomol Ther. 2013; 21(2): 170-172. (Year: 2013).*
Anand et al. Biochemical Education. 1992; 20(3): 183-184. (Year: 1992).*
Anonymous. Nutri Avenue [online]; 2017; downloaded from <URL https://www.nutriavenue.com/magnesium-beta-hydroxybutyrate-the-ketone-compound-for-diabetic-patients/ > on Nov. 9, 2024; 3 pages. (Year: 2017).*
Nakamura et al. Invest Ophthalmol Vis Sci. 2003; 44: 4682-4688. (Year: 2003).*
Choi et al. Neuroscience Research. 2006; 56: 111-118. (Year: 2006).*
Nair and Jacob. J Basic Clinical Pharm. 2016: 7: 27-31. (Year: 2016).*
Achanta et al., "[Beta]-Hydroxybutgtyrate in the Brain: One Molecule, Multiple Mechanisms", Neurochem. Res. (Jan. 2017). 42(1): 35-49.
Bazzigaluppi, "Imaginng the Effects of [Beta]-Hydroxybutyrate on Peri-Infarct Neurovascular Function and Metabolism", Stroke (Sep. 2018). 49: 2173-2181.
Bowen-Pope et al., "Magnesium and calcium effects on uptake of hexoses and uridine by chick embryo fibroblasts", Proc. Natl. Acad. Sci. USA (Apr. 1977). 74(4): 1585-1589.

(Continued)

*Primary Examiner* — David Browe
(74) *Attorney, Agent, or Firm* — MEDLER FERRO WOODHOUSE & MILLS PLLC

(57) ABSTRACT

A solution of uridine in saline, and optionally also containing beta-hydroxybutyrate, can be administered subcutaneously. A reservoir capable of holding a uridine solution in saline is described, the reservoir being fluidically linked to one or more infusion needles, and a pump configured to move the solution from the reservoir through the one or more infusion needles into a subject.

12 Claims, 9 Drawing Sheets

(56)          References Cited

OTHER PUBLICATIONS

Cook et al., "The role of magnesium in CNS injury", in Magnesium in the Central Nervous System (Vink et al., eds., U. Adelaide Press 2011) Ch. 12, pp. 167-179.

Frey et al., "The addition of ketone bodies alleviates mitochondrial dysfunction by restoring complex I assembly in a MELAS cellular model", Biochimica et Biophysica Acta (2017). 1863: 284-291.

Goren et al., "Long-term cognitive effects of uridine treatment in a neonatal rat model of hypoxic-ischemic encephalopathy", Brain Research (2017). 1659: 81-87.

Lim et al., "D-[beta]-Hydroxybutyrate Is Protective in Mouse Models of Huntington's Disease", PLoS One (Sep. 2011). 6(9): e24620, pp. 1-10.

Meloni et al., "The use of magnesium in experimental cerebral ischemia", in Magnesium in the Central Nervous System (Vink et al. eds., U. Adelaide Press 2011) Ch. 13, pp. 181-193.

Rubin, "Intracellular free Mg2+ and MgATP2− in coordinate control of protein synthesis and cell proliferation", in Magnesium in the Central Nervous System (Vink et al. eds., U. Adelaide Press 2011) Ch. 4, pp. 75-84.

Cansev et al., "Neuroprotective effects of uridine in a rat model of neonatal hypoxic-ischemic encephalopathy", Neuroscience Letters. (2013). 542: 65-70.

Enders et al., "The Role of [Beta]-Hydroxybutyrate as a Neuroprotective Substance During Hypoxia/Ischemia: A 31P NMR Study in the Unanesthetized Neonatal Rat", International Society for Magnetic Resonance in Medicine (ISMRM). (Aug. 14, 1993). p. 1489.

Brunner et al., "Enhancement of Ketone Supplements-Evoked Effect on Absence Epileptic Activity by Co-Administration of Uridine in Wistar Albino Glaxo Rijswijk Rats," Nutrients 13(1):234 (2021).

Shimada et al., "RNA Synthesis In The Neurons Of The Brain Of Mouse And Kitten As Visualized By Autoradiography After Injection Of [³H]Uridine," Journal of Neurochemistry 13(5):391-396 (1966).

Van Groeningen et al., "Clinical and pharmacokinetic studies of prolonged administration of high-dose uridine intended for rescue from 5-FU toxicity," Cancer treatment reports 70(6):745-750 (1986).

Van Groeningen et al., "Clinical and pharmacologic study of orally administered uridine," Journal of the National Cancer Institute, 83(6), 437-441 (1991).

Nair and Jacob, "A simple practice guide for dose conversion between animals and human," J Basic Clin Pharm 7(2):27-31 (2016).

* cited by examiner

COMPOSITIONS AND DEVICES FOR SYSTEMIC DELIVERY OF URIDINE

BACKGROUND OF THE INVENTION

Brain injury caused by trauma or oxygen deprivation is a major cause of irreversible morbidity and mortality. Traumatic brain injury (TBI) and hypoxic-ischemic encephalopathy (HIE) display similar courses of damage and recovery, in that the initial insult (whether traumatic or ischemic), once stabilized, is often followed by a phase of metabolic crisis and consequent secondary injury beginning minutes to a few days after the initial insult, which may include mitochondrial failure, edema (with consequent impaired cerebral blood perfusion due to increased intracranial pressure), seizures, excitotoxic injury, cell death, and inflammation. This secondary phase often contributes to long-term or irreversible consequences, including mortality, after initiation of HIE and TBI, but also provides a time window wherein neuroprotective agents or procedures (such as cerebral hypothermia) can be applied to attenuate cumulative damage and promote recovery.

Intraperitoneal injections of uridine have been shown to display some degree of neuroprotective effects in rodent models of TBI and HIE, reducing cell death and brain swelling. However, most or all such studies have been performed in rats, which rapidly and extensively catabolize uridine (using cytidine instead for interorgan pyrimidine transfer) and therefore do not predict the potential activity (or lack of activity) of uridine in humans or other species. Uridine can also induce hypothermia in rats as a consequence of its degradation, potentially confounding interpretation of protective results, as hypothermia induced by cooling the head or the body can display some neuroprotective activity, as it can reduce tissue energy demands In humans, systemic uridine administration was abandoned in clinical trials after problems were encountered in attempts to administer uridine by intravenous infusion. Hyperthermia was encountered as a dose-limiting toxicity during intravenous uridine infusion in humans (in contrast to a hypothermic effect in rodents); hyperthermia is counterproductive in subjects with brain injury and may exacerbate damage in acute brain trauma or ischemia. Furthermore, uridine infusion into accessible peripheral veins in humans caused local phlebitis, and administration via central venous catheters was required to overcome this side effect. For these reasons, parenteral uridine administration was abandoned in favor of the orally-bioavailable uridine prodrug uridine triacetate as a method for delivering systemic uridine in the early 1990s.

Alternative fuels for supporting brain energy metabolism after TBI or HIE have been proposed, but have also shown equivocal results in animal models. Beta-hydroxybutyrate (BHB), a ketone body that the brain can use directly in situations of reduced glucose availability or impaired glucose utilization, has shown both positive and deleterious effects in models of cerebral injury, including damage to the integrity of the blood-brain barrier when given in neuroprotective doses by intravenous infusion, e.g. at 30 mg/kg BHB for 6 hours in rats.

A variety of other agents have been tested with the intention of reducing secondary brain damage after TBI or HIE, including magnesium, which has shown equivocal, and sometimes deleterious, results in preclinical animal models and little or no benefit in human clinical trials. Magnesium transport across the blood-brain barrier may limit its usefulness, and it is not clear whether magnesium deficits observed in the brain after TBI and in other pathological situations is a cause or an effect of cellular damage or energy failure. A review of clinical experience with magnesium treatment in TBI concluded, "There is no evidence to support the use of magnesium salts in patients with acute traumatic brain injury" (Arango M F and Bainbridge D, "Magnesium for acute traumatic brain injury (Review). Cochrane Database of Systematic reviews 2008, Issue 4, Article NO. CD005400)

SUMMARY OF THE INVENTION

This invention provides a solution comprising a neuroprotective amount of uridine dissolved in saline solution.

This invention provides a method of treating an acute brain injury condition in a subject, comprising administering to the subject a composition comprising neuroprotective amount of uridine dissolved in saline solution.

This invention provides a system for delivery of uridine, comprising a reservoir capable of holding a solution comprising uridine dissolved in saline, the reservoir being fluidically linked to one or more infusion needles, and a pump configured to move the solution from the reservoir through the one or more infusion needles into a subject.

This invention provides a method of administering uridine to a mammalian subject in need of uridine therapy, comprising administering subcutaneously to the subject a pharmaceutical composition comprising uridine dissolved in a saline solution, in an amount sufficient to maintain a plasma uridine concentration of 50 to 150 micromolar in the subject.

DETAILED DESCRIPTION OF THE INVENTION

Figure 1:
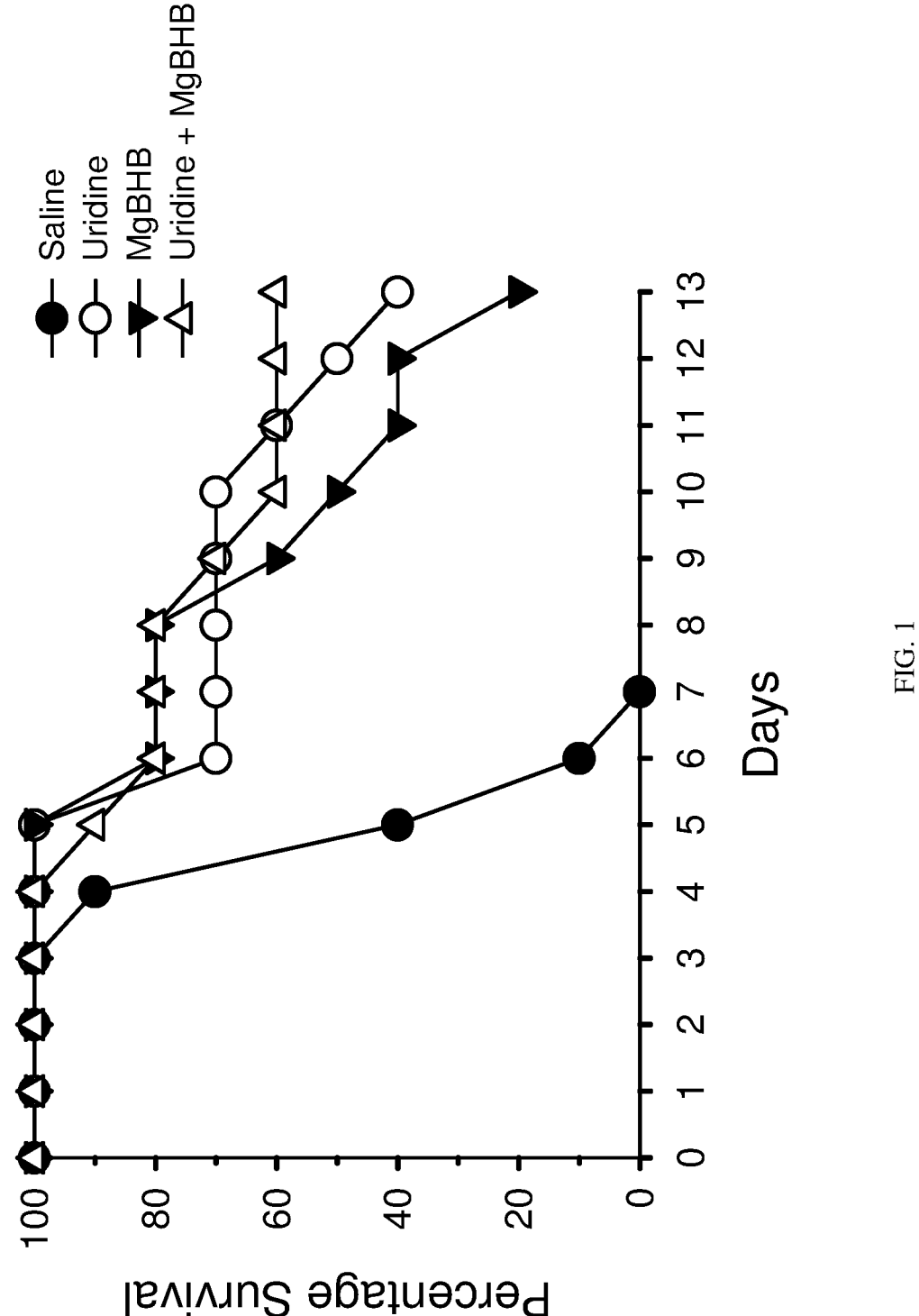
FIG. 1: Effect of Uridine and Racemic MgBHB (magnesium β-hydroxybutyrate) on Mortality in Mice Treated with 60 mg/Kg 3-NP (3-nitropropionic acid). In a 3-NP mouse model of mitochondrial dysfunction the percent survival at various time points is shown for mice treated with saline (negative control), subcutaneous uridine solution, MgBHB·3H$_2$O, or both subcutaneous uridine solution and MgBHB·3H$_2$O.

In emergency situations such as traumatic brain injury (TBI) and hypoxic-ischemic encephalopathy (HIE)—a consequence of birth asphyxia—or resuscitation after cardiac arrest or drowning, initiation of neuroprotective therapy as rapidly as possible is essential, and placement of a central venous catheter is problematic and hazardous in such situations, especially when other injuries that often accompany TBI require immediate attention.

If a victim of TBI or HIE is unconscious or otherwise incapacitated, an oral uridine prodrug such as uridine triacetate may be difficult to administer properly, especially in an emergency situation, where time to treatment is crucial.

There exists a need for rapid, controlled administration of systemic uridine in concentrations and for durations sufficient to protect the brain and other tissues without deleterious side effects such as hyperthermia or phlebitis, and without requiring central venous access for administration.

Uridine has been reported to provide neuroprotection in some models of mitochondrial dysfunction and acute hypoxia and ischemia when delivered as oral uridine triacetate or as intraperitoneal injections of uridine itself. For some emergency clinical indications such as birth asphyxia, stroke, or traumatic brain injury, a subcutaneous route of delivery is potentially advantageous, though it has not heretofore been established that uridine delivery to the systemic circulation and brain rapidly enough and in quantities sufficient for neuroprotection is feasible by this route of administration. The efficacy of subcutaneous uridine in a model of severe energy failure has not been reported previously. Furthermore, the therapeutic activity of other putative neuroprotective agents has not previously been tested head-to-head with uridine, nor has a combination of such agents coadministered in a subcutaneous formulation been tested to determine if there are additive or supra-additive benefits of such combinations.

Subcutaneous Uridine Infusion Device

Despite problems encountered with intravenous administration of uridine to humans, for emergency administration of systemic uridine, subcutaneous infusion of uridine dissolved in physiological saline is effective and practical. Unlike many drugs and biological agents, uridine distributes rapidly into total body water and is not bound to subcutaneous tissues.

In one embodiment, an infusion device dispenses liquid at a controlled rate via one or more short, low-diameter infusion needles; in some embodiments, the needles are arrayed in an adhesive patch that secures them in place after insertion into the skin. The patches are applied to skin, e.g. on the abdomen, and uridine at an appropriate concentration is infused at a rate that provides adequate concentrations in plasma to produce neuroprotective effects in the central nervous system. Uridine in the circulation crosses the blood-brain barrier via nucleoside transporters at a rate adequate to provide neuroprotective effects, if sufficient plasma concentrations are maintained for a sufficient duration of time.

For emergency use, infusion devices that do not require an external power source are advantageous in some situations, especially outside of hospitals. Infusion devices that do not require electric power are known in the art. In one embodiment, uridine is infused via a mechanical ("spring-driven") or elastomeric infusion device providing a controlled rate of administration over an adequate time period. Electric pumps, including battery-powered pumps, are included within the scope of the invention.

Pumps with adjustable flow rates, or alternatively pumps with reservoirs of different sizes permit optimization of infusion rate to treat patients with different body sizes, ranging from neonates (and even preterm infants) to adults, so that plasma uridine is maintained in the proper therapeutic zone for protecting the brain and other tissues.

In some embodiments, a single injection rather than an infusion of uridine is an important option, for example, an injection given under emergency conditions by first responders prior to hospitalization. Under such conditions, a subcutaneous injection that can be readily administered from a small portable device such as a preloaded syringe, can provide neuroprotection that attenuates cell dysfunction and death during the time required for transportation to a hospital or for a more complete evaluation to determine the course of treatment. A stroke depriving the brain of blood or oxygen may be ischemic or hemorrhagic. Agents that dissolve a thrombus are appropriate for ischemic strokes but are potentially lethal in people with hemorrhagic strokes. Differentiation of ischemic from hemorrhagic strokes generally requires imaging equipment at hospitals. Compositions of the invention may be safely administered to provide neuroprotection regardless of whether a stroke is ischemic or hemorrhagic, preserving tissue until a determination of the stroke type and treatment can take place.

Subcutaneous Infusion Compositions

In addition to uridine, other neuroprotective agents are optionally included in the subcutaneous uridine infusion solution. The constraints are that such constituents should be soluble and readily diffuse from the infusion site into total body water, including the circulation.

Organic anions are also optionally included in the uridine infusion solution. Such anions include but are not limited to beta-hydroxybutyrate (also called 3-hydroxybutyrate), threonine, aspartate or other amino acids, gluconate, pyroglutamate, citrate, ketoleucine, acetate and lactate. Beta-hydroxybutyrate (BHB), a ketone body that the brain can utilize as an alternative fuel, is an advantageous anion, as BHB has been reported to have some neuroprotective effects. One potential consequence of its use is that BHB can inhibit de novo synthesis of uridine nucleotides, acting against its net protective effects. Coadministration of uridine with BHB overcomes this potential problem and the protective effect of a combination was also found to be markedly more effective in animal models of acute mitochondrial energy failure than was either component alone, with supra-additive effects on survival and morbidity. Racemic BHB or, preferably, the D enantiomer of BHB can be used. The D enantiomer of BHB is also known as the R enantiomer in the (R)-(S) nomenclature system. The D enantiomer of BHB can be referred to as D-BHB, (R)-BHB, (R)-(−)-BHB, (R)-(−)-3-Hydroxybutyrate, (R)-(−)-β-Hydroxybutyrate, D-(−)-β-Hydroxybutyrate, among other names known to those of skill in the art.

Organic anions require cationic counterions, so that the composition has a pH within a physiologically tolerable range, preferably pH 5 to 7.5. Sodium ions (Na+) and magnesium ions ($Mg^{2+}$) are suitable cations. Magnesium ions may have some neuroprotective and tissue protective attributes, adding to the overall benefit of compositions of the invention. However, there are upper limits on the amount of magnesium that may be administered as an acute dose, as plasma concentrations exceeding 4 mEq per liter can cause side effects such as impairment of deep tendon reflexes, and higher concentrations can cause hypotension and heart block. Thus, for a single injection for emergency treatment, the sodium salt of BHB is preferred, or a mixture of magnesium and sodium ions is administered, capping the magnesium dose at 40 mEq (1 gram of Mg ions) per injection in a human adult or 10 mEq (0.25 gram of Mg ions) per injection in a human child, with the remainder of BHB, if any, balanced with sodium as the counterion. For prolonged infusions of compositions of the invention, which generally result in lower peak concentrations of the infused agents, sodium BHB or a mixture of sodium BHB and magnesium BHB is administered, in which case the Mg dose is capped at 80 mEq per day (40 mEq in a 12 hour period) in an adult or 40 mEq per day (20 mEq per 12 hour period) in a child, with the remainder of the counterions for BHB comprising sodium ions.

The infusion solution need not be isotonic; solutions with osmolalities up to approximately 800 milliosmoles per liter are known to be acceptable for subcutaneous administration in humans. Hypertonic solutions up to an acceptable limit minimize the total fluid volume that must be administered.

A local anesthetic, including but not limited to lidocaine or lignocaine, is optionally added to a composition of the invention up to a maximum of 2% w/v, preferably 0.4 to 1%, to minimize local discomfort or pain following an injection or infusion via the subcutaneous route.

Hypothermia induced by surface cooling, with intravascular heat-exchange catheters, or by infusion of cold fluids, has neuroprotective effects in subjects after TBI, HIE or cardiac arrest. Pharmacologic hypothermia, induced by administration of agents that affect thermoregulation and reduce body or brain temperature also can protect the brain and other tissues after trauma or ischemic injury. Pharmacologic hypothermia is especially important in situations where sophisticated cooling equipment is not available. Hypothermic agents are optionally incorporated into a composition of this disclosure. Suitable hypothermic agents include A3 adenosine receptor agonists (selective or nonselective), 5-HT (serotonin) 1 A receptor agonists, activators of "warming" transient receptor potential channel, especially activators of TRPV1 (e.g. dihydrocapsaicin or rinvanil), TRPV3 (e.g. carvacrol), and optionally inhibitors of the "cooling" TRP channel TRPM8. Such agents are administered in doses and at infusion rates that reduce body or brain temperature with an acceptable safety and tolerability profile. Concurrent magnesium infusion can reduce compensatory shivering responses and thereby improve both hypothermic effects and patients' comfort.

Concentrations and Volumes

The concentrations of uridine and other components of the infusion solution are interrelated with flow rates, diffusion from subcutaneous spaces, and the size of the reservoir of the infusion device.

The pharmacokinetic goal of subcutaneous uridine infusion is to maintain plasma uridine within a concentration band of 50 to 150 micromolar. Subcutaneous infusion of 0.5 to 2 grams/m² per hour of uridine in solution is suitable for maintaining plasma uridine within this therapeutic zone. In some embodiments, infusional delivery is pulsatile, with periodically increased infusion rates and corresponding increases in plasma uridine and BHB, with plasma uridine concentrations in the range of 200 to 500 micromolar, more specifically 300 to 500 micromolar, for approximately one hour, with 2 to 4 such peaks in each 24 hour period of infusion. Similarly, in embodiments in which compositions of the invention are administered by subcutaneous injection rather than a prolonged infusion, doses and concentrations are gauged to achieve peak plasma uridine concentrations of 200 to 500 micromolar, or more specifically 300 to 500 micromolar.

Uridine is extremely soluble in water (room temperature solubility >50%, or >0.5 g/ml), permitting infusion of relatively low volumes if desired. For example, delivery of 1 gram/m² based on body surface area (BSA) per hour of uridine for 12 hours in a typical adult (BSA approximately 1.6 m²) could be accomplished with a total infusion volume of less than 40 or 50 ml, an amount that can be readily introduced into and absorbed from subcutaneous spaces over that time period.

Magnesium ion concentrations in the infusion solution are based on the infusion rates determined to provide optimum exposure to plasma uridine. In embodiments where magnesium ions are used as a counterion to beta-hydroxybutyrate, in the case of an adult the preferred dose of magnesium ions is 10 to 40 milliEquivalents of magnesium ions per 12 hours, advantageously 20 to 30 mEq per 12 hours, or twice these amounts per 24 hour period of infusion. In the case of a child the preferred dose of magnesium ions is 10 to 20 milliEquivalents of magnesium ions per 12 hours, or twice this amount per 24 hour period of infusion.

After the initial 12 hour infusion, additional 12 hour infusions are optionally initiated sequentially as needed, depending on the condition of the patient as assessed by appropriate instrumental neurocritical care monitoring techniques, plasma or serum markers of brain injury or clinical signs.

For single-dose injections as an alternative to prolonged infusions, the composition of the invention comprises sufficient uridine or uridine plus a metal salt of BHB, to deliver 10 to 40 mg/kg body weight uridine in a single dose and 0 to 100 mg/kg BHB, preferably 50 to 100 mg/kg, at aggregate concentrations that do not exceed 800 milliosmoles per liter. In a 70 kg adult, these dose ranges would be equivalent to 700 to 2800 mg of uridine and 0 to 7000 mg of D-BHB, more specifically 4000 to 7000 mg of D-BHB. In a 3 kg newborn child, a single dose of a composition of the invention would comprise 30 to 120 mg uridine and 0 to 300 mg D-BHB, more specifically 100 to 300 mg D-BHB. In embodiments of injection according to this invention where magnesium ions are used as a counterion to beta-hydroxybutyrate, the preferred dose of magnesium ions is from 10 to 40 milliEquivalents in the case of an adult and from 5 to 10 milliEquivalents in the case of a child.

Peripheral Tissue Damage in Hypoxic Ischemic Encephalopathy

Hypoxic-ischemic encephalopathy (HIE) is defined by brain injury and dysfunction caused by perinatal cerebral asphyxia or ischemia, which may be caused by umbilical cord compression, placental abruption, failure to start breathing immediately after birth, or perinatal infection. HIE is a major cause of infant mortality and long-lasting disabilities including cerebral palsy, developmental delays and seizure disorders.

Infants, especially preterm, may not be able to receive oral medications immediately, due to either intestinal immaturity or risk of triggering intestinal complications such as necrotizing enterocolitis.

Subcutaneous infusion of a uridine solution presents a method for rapidly introducing systemic uridine that can gain access to the brain via the circulation in newborn infants subjected to birth asphyxia. Furthermore, HIE is very commonly accompanied by peripheral organ dysfunction or failure due to hypoxia, ischemia or inflammation. Uridine protects peripheral tissues against hypoxia and inflammation, and thereby has additional benefits in HIE beyond its neuroprotective effects when administered to a neonate recovering from asphyxia. Similarly, TBI is often accompanied by injury to peripheral tissues, due to trauma, hemodynamic problems or inflammation. Infusion solutions of this disclosure comprising uridine protect peripheral tissues during recovery from TBI.

An embodiment of the pharmaceutical composition of this invention further comprises a neuroprotective amount of beta-hydroxybutyrate and a cationic counterion. In a preferred embodiment the beta-hydroxybutyrate and counterion are in the same solution as the uridine. In embodiments of this invention the beta-hydroxybutyrate is the D enantiomer of beta-hydroxybutyrate or a mixture of the D and L enantiomers, for example racemic beta-hydroxybutyrate. In accordance with this invention any conventional cationic counterion can be utilized. In one embodiment the cationic counterion is $Na^+$. In another embodiment both $Na^+$ and $Mg^{2+}$ are present as counterions.

In an embodiment of this invention the solution further comprises an organic anion selected from the group consisting of, an amino acid, gluconate, pyroglutamate, citrate, acetate, and lactate. Examples of suitable amino acids include threonine or aspartate. In an embodiment of this invention the solution further comprises a hypothermic agent. In an embodiment of this invention the saline solution is isotonic or hypertonic saline. In an embodiment of this invention the pharmaceutical composition is formulated for subcutaneous administration to a subject.

In an embodiment of this invention the pharmaceutical composition is formulated for subcutaneous infusion. In a more specific embodiment the amount of uridine is sufficient to maintain plasma uridine at a concentration from 50 to 150 micromolar in a human subject to whom the pharmaceutical composition is administered. In another embodiment the amount of uridine is sufficient to maintain plasma uridine at a concentration from 200 to 500 micromolar for about one hour in a human subject to whom the pharmaceutical composition is administered. An embodiment of the pharmaceutical composition for subcutaneous infusion further comprises from 100 to 300 mg of the D enantiomer of beta-hydroxybutyrate and a cationic counterion. In a more specific embodiment the subject is a human adult, wherein the cationic counterion comprises $Mg^{2+}$ in an amount to deliver from 10 to 40 milliEquivalents of $Mg^{2+}$ in a twelve-hour delivery period. Alternatively the subject is a human child, for example a newborn infant, wherein the cationic counterion comprises $Mg^{2+}$ in an amount to deliver from 10 to 20 milliEquivalents of $Mg^{2+}$ in a twelve-hour delivery period.

In an embodiment of this invention the pharmaceutical composition is formulated for subcutaneous injection. In a more specific embodiment the amount of uridine is sufficient to maintain plasma uridine at a concentration from 200 to 500 micromolar for about one hour in a human subject to whom the pharmaceutical composition is administered.

In an embodiment of the pharmaceutical composition formulated for subcutaneous injection the subject is a human adult and the amount of uridine is from 10 to 40 mg/kg. A more specific embodiment comprises from 50 to 100 mg/kg of the D enantiomer of beta-hydroxybutyrate and a cationic counterion. In a more specific embodiment the cationic counterion comprises $Mg^{2+}$ in an amount of from 10 to 40 milliEquivalents.

In another embodiment of the pharmaceutical composition formulated for subcutaneous injection the subject is a human child and the amount of uridine is from 30 to 120 mg.

A more specific embodiment further comprises from 100 to 300 mg of the D enantiomer of beta-hydroxybutyrate and a cationic counterion. In a more specific embodiment the cationic counterion comprises Mg2+ in an amount of from 5 to 10 milliEquivalents.

In an embodiment of this invention the pharmaceutical composition is for treatment of a patient having an acute brain injury condition. In more specific embodiments the acute brain injury condition is selected from the group consisting of traumatic brain injury, birth asphyxia, hypoxic-ischemic encephalopathy, stroke, brain jury from cardiac arrest, and brain injury from drowning.

An embodiment of the method of treating an acute brain injury of this invention further comprises administering a neuroprotective amount of beta-hydroxybutyrate and a cationic counterion. In a preferred embodiment the beta-hydroxybutyrate and counterion are in the same solution as the uridine. In embodiments of this invention the beta-hydroxybutyrate is the D enantiomer of beta-hydroxybutyrate or a mixture of the D and L enantiomers, for example racemic beta-hydroxybutyrate. In accordance with this invention any conventional cationic counterion can be utilized. In one embodiment the cationic counterion is $Na^+$. In another embodiment both Na and $Mg^{2+}$ are present as counterions.

In an embodiment of the method of this invention the solution further comprises an organic anion selected from the group consisting of, an amino acid, gluconate, pyroglutamate, citrate, acetate, and lactate. Examples of suitable amino acids include threonine or aspartate. In an embodiment of this invention the solution further comprises a hypothermic agent. In an embodiment of this invention the saline solution is isotonic or hypertonic saline. In an embodiment of this invention the pharmaceutical composition is administered subcutaneously.

In an embodiment of this invention the administration is by subcutaneous infusion. In a more specific embodiment the amount of uridine is sufficient to maintain plasma uridine at a concentration from 50 to 150 micromolar. In another embodiment the amount of uridine is sufficient to maintain plasma uridine at a concentration from 200 to 500 micromolar for about one hour. An embodiment of the method further comprises administering from 100 to 300 mg of the D enantiomer of beta-hydroxybutyrate and a cationic counterion. In a more specific embodiment the subject is a human adult and the cationic counterion comprises $Mg^{2+}$ in an amount to deliver from 10 to 40 milliEquivalents of $Mg^{2+}$ in a twelve-hour delivery period. Alternatively the subject is a human child, for example a newborn infant, and the cationic counterion comprises $Mg^{2+}$ in an amount to deliver from 10 to 20 milliEquivalents of $Mg^{2+}$ in a twelve-hour delivery period.

In an embodiment of this invention the administration is by subcutaneous injection. In a more specific embodiment the amount of uridine is sufficient to maintain plasma uridine at a concentration from 200 to 500 micromolar for about one hour in a human subject.

In an embodiment of the method in which administration is by subcutaneous injection the subject is a human adult and the amount of uridine is from 10 to 40 mg/kg. A more specific embodiment further comprises administering from 50 to 100 mg/kg of the D enantiomer of beta-hydroxybutyrate and a cationic counterion. In a more specific embodiment the cationic counterion comprises $Mg^{2+}$ in an amount of from 10 to 40 milliEquivalents.

In another embodiment of the method in which administration is by subcutaneous injection the subject is a human child and the amount of uridine is from 30 to 120 mg. A more specific embodiment further comprises administering from 100 to 300 mg of the D enantiomer of beta-hydroxybutyrate and a cationic counterion. In a more specific embodiment the cationic counterion comprises Mg2+ in an amount of from 5 to 10 milliEquivalents.

In accordance with this invention any the acute brain injury condition treated in can be any acute brain injury. In more specific embodiments the acute brain injury condition is selected from the group consisting of traumatic brain injury, birth asphyxia, hypoxic-ischemic encephalopathy, stroke, brain jury from cardiac arrest, and brain injury from drowning.

The invention will be better understood by reference to the following examples, which illustrate but do not limit the invention described herein.

Example 1: Protection Against Mortality Caused by 3-Nitropropionic Acid, an Inihibitor of Mitochondrial Respiration 3-nitropropionic acid (3-NP) is an inhibitor of Complex II of the mitochondrial respiratory chain. Administration of 3-NP to experimental animals has been used as a model for mitochondrial diseases, Huntington's disease and pathological consequences of hypoxia. Daily dosing with 3-NP causes energy failure in the brain, heart and other tissues, resulting in mortality after several days. A 3-NP dosing regimen that caused 100% mortality in mice after approximately one week was selected for further evaluation of mortality, which is indicative of neuroprotective and cardioprotective effects, of compositions of the invention in a model of disorders caused by mitochondrial dysfunction. Survival times (median survival; the time point at which 50% of animals in a group had died) and percent survival at the end of the 13 day study were used to quantify protective effects of the test agents.

Female CD-1 mice at approximately 16 weeks of age were divided into weight-matched groups of 10 mice each. All mice received daily intraperitoneal injections of 3-NP (60 mg/kg) in a volume of 0.01 ml per gram of body weight. 3-NP was administered at 2 PM on each of the 13 consecutive days of the experiment. Body weights were recorded each day to adjust drug doses as mice lost weight during repeated treatment with 3-NP.

The comparative efficacy of uridine (VWR International) and the magnesium salt of racemic beta-hydroxybutyrate (magnesium β-hydroxybutyrate trihydrate; MgBHB·3H$_2$O) (Nutra Planet) were assessed, as was the efficacy of a combination of uridine and MgBHB. All of the therapeutic treatments were administered by subcutaneous injection in a volume of 0.02 ml/gram of body weight twice per day, at 7 AM and 1 PM.

Groups:

1. Vehicle Control—0.9% saline b.i.d.

2. Uridine 300 mg/kg b.i.d.

3. MgBHB 300 mg/kg b.i.d.

4. Uridine 300 mg/kg+MgBHB 300 mg/kg b.i.d.

Results:

Mice in the Vehicle Control group began to die on Day 4 after initiation of 3-NP dosing, and all mice in the entire group died by Day 7. The final survival percentages and median survival times at the end of the 13 day study are shown in the table below and in FIG. 1.

TABLE 1

| Survival of mice receiving 60 mg/kg/day 3-nitropropionic acid and treated with subcutaneous uridine 300 mg/kg b.i.d. and MgBHB 300 mg/kg b.i.d. alone and in combination | | |
| --- | --- | --- |
| Group | % Survival | Median Survival |
| Vehicle Control | 0% (0/10) | 5 Days |
| Uridine | 40% (4/10) | 12 Days |
| MgBHB | 20% (2/10) | 10 Days |
| Uridine + MgBHB | 60% (6/10) | >13 Days |

These results indicate that the subcutaneous administration of uridine alone provided substantial protection against the lethal toxicity of repeat-dose 3-NP. MgBHB provided some protection, but less than that of uridine. The combination of uridine and MgBHB was superior to either uridine or MgBHB alone.

Example 2: Protection Against Mortality Caused by 3-Nitropropionic Acid by Uridine and Sodium Beta-Hydroxybutyrate Alone and in Combination Uridine and beta-hydroxybutyrate (BHB) both independently display protective effects against toxicity and mortality caused by repeated daily dosing with 3-nitropropionic acid, an inhibitor of Complex II of the mitochondrial respiratory chain. BHB is an endogenous ketone body which can be used as a metabolic fuel by the brain. The D isomer of BHB is the form produced as a product of lipid and amino acid metabolism. When BHB is produced industrially, it is often made as a DL entantiomeric mixture, which is simpler to synthesize than is the pure D isomer. L-BHB can be enzymatically converted to D-BHB in vivo, so that both D- and DL-BHB may provide equivalent calories of usable energy. However, the relative activity of D versus DL BHB for protection against energy failure in disorders associated with impaired mitochondrial function has not been established, especially when either form of BHB is combined with a source of uridine.

Mitochondrial dysfunction was produced by daily administration of 3-nitropropionic acid (60 mg/kg/day) by intraperitoneal injection. Groups of mice also received saline (control), uridine, DL-BHB, D-BHB, and combinations of uridine and D-BHB and DL-BHB as indicated below. Both D- and DL-BHB were administered as the water soluble sodium salts: Na(D-BHB) (Toronto Research Chemicals, catalog #H833025) and Na(DL-BHB) (VWR International, catalog #200012-200).

Groups:

1. Vehicle Control—0.9% saline b.i.d.

2. Uridine 200 mg/kg t.i.d.

3. Na (DL-BHB) 328 mg/kg t.i.d.

4. Na (D-BHB) 328 mg/kg t.i.d.

5. Uridine 200 mg/kg+Na (DL-BHB) 328 mg/kg t.i.d.

6. Uridine 200 mg/kg+Na (D-BHB) 328 mg/kg t.i.d.

Survival times (median survival; the time point at which 50% of animals in a group had died) and percent survival at the end of the 12 day study were used to quantify and compare protective effects of the test agents.

Female CD-1 mice at approximately 16 weeks of age were divided into weight-matched groups of 10 mice each. All mice received daily intraperitoneal injections of 3-NP (60 mg/kg) in a volume of 0.01 ml per gram of body weight at 5 PM.

The therapeutic treatments were administered by subcutaneous injection in a volume of 0.01 ml/gram of body weight three times per day, at 7 AM and 12 PM and 4 PM. 3-NP was administered at 5 PM on each of the consecutive days of the experiment. Body weights were recorded each day to adjust drug doses as mice lost weight during repeated treatment with 3-NP. Body weight was graphed for the various groups of mice until the group size decreased below 3.

Figure 2:
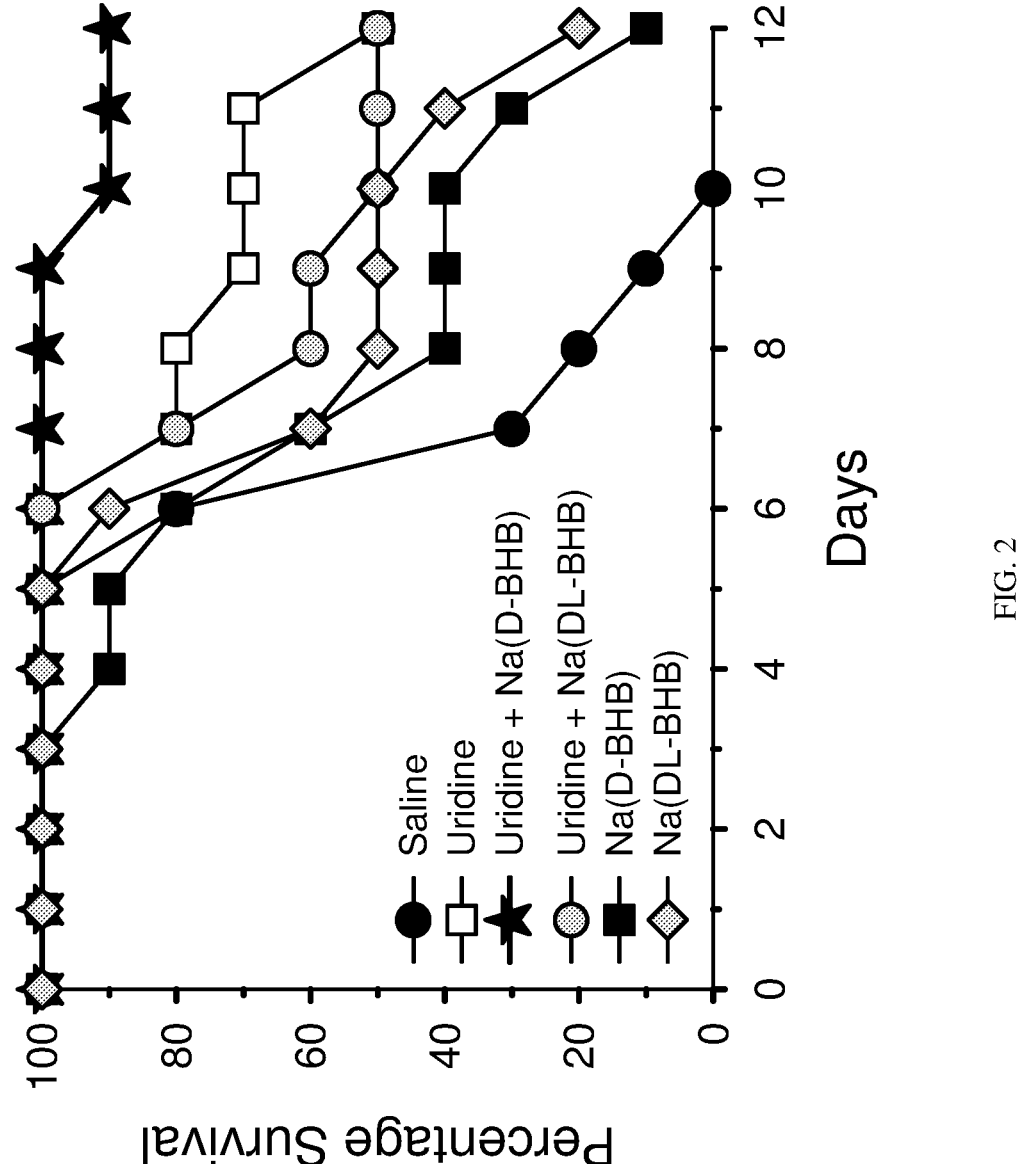
FIG. 2: Survival of mice receiving 60 mg/kg/day 3-nitropropionic acid and treated with subcutaneous uridine 200 mg/kg t.i.d. and Na(D-BHB) versus Na(DL-BHB) 328 mg/kg t.i.d., alone and in combination

Results:

The final survival percentages and median survival times at the end of the study are shown in the following table and in FIG. 2.

TABLE 2

Survival of mice receiving 60 mg/kg/day 3-nitropropionic acid and treated with subcutaneous uridine 200 mg/kg t.i.d. and Na(DL-BHB) or Na(D-BHB) 328 mg/kg t.i.d. alone and in combination

| Group | % Survival | Median Survival |
|---|---|---|
| Vehicle Control | 0% (0/10) | 6.5 Days |
| Uridine | 50% (5/10) | 12 Days |
| Na (DL-BHB) | 20% (2/10) | 8 Days |
| Na (D-BHB) | 10% (1/10) | 7.5 Days |
| Uridine +Na (DL-BHB) | 50% (5/10) | 10 Days |
| Uridine +Na (D-BHB) | 90% (9/10) | >12 Days |

Figure 3:
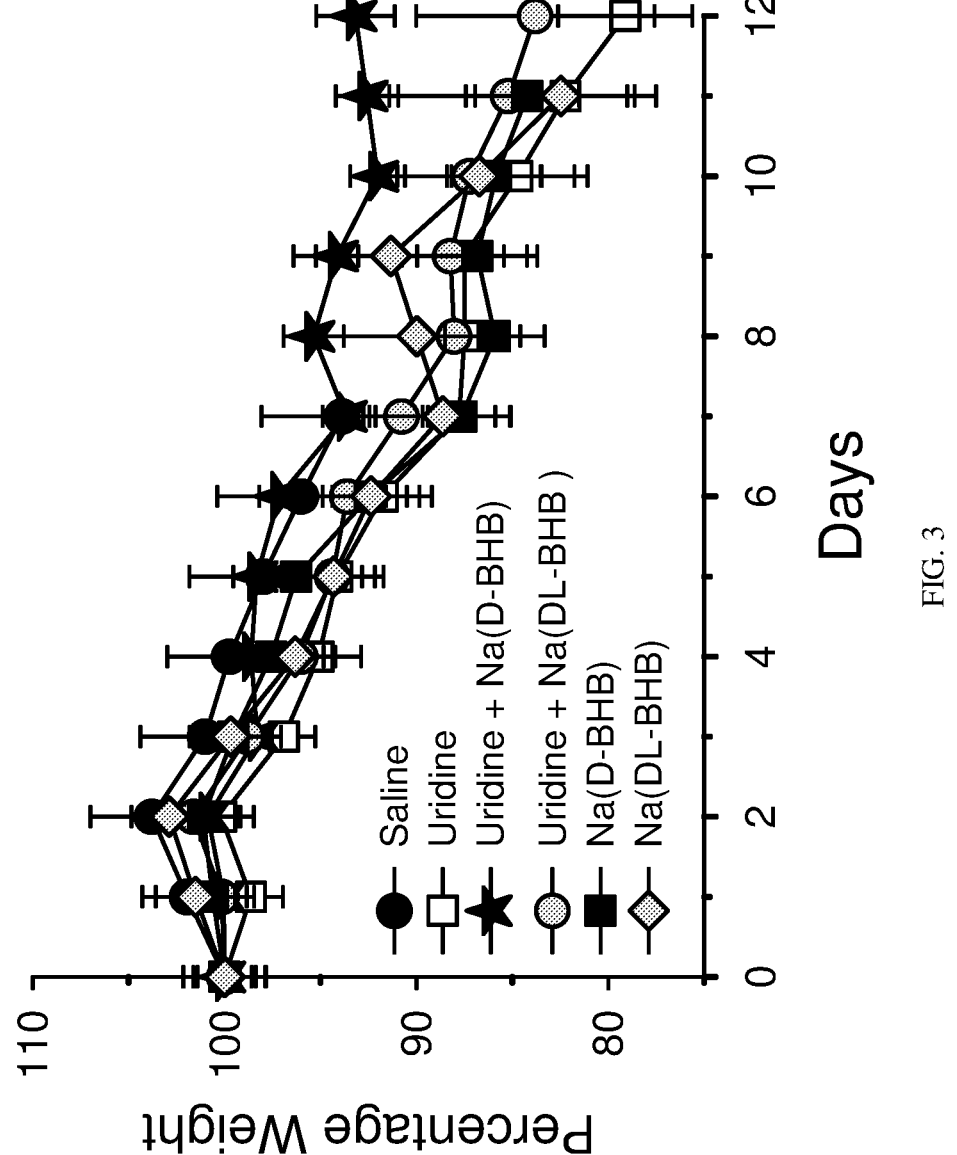
FIG. 3: Body weight change (% of baseline weight) in mice receiving 60 mg/kg/day 3-nitropropionic acid and treated with subcutaneous uridine 200 mg/kg t.i.d. and Na(D-BHB) versus Na(DL-BHB) 328 mg/kg t.i.d., alone and in combination

These results indicate that the subcutaneous administration of uridine alone provided substantial protection against the lethal toxicity of repeat-dose 3-NP. Na(DL-BHB) and Na(D-BHB) both individually provided some protection against mortality, and were not significantly different from each other, with median survival times of 7.5 (final survival 20%) and 8 days (final survival 10%) respectively. Uridine alone permitted 50% survival, with a median survival time of 12 days. Na(DL-BHB) did not enhance the protective effect of uridine at the end of the experiment, with a final survival of 50% with the combination of uridine and Na(DL-BHB), and with a median survival time was 10 days. In contrast, Na(D-BHB) given with uridine resulted in 90% survival at the end of the study. Furthermore, the combination of uridine with Na(D-BHB) protected against body weight loss better than did any of the single agents or the combination of uridine and Na(DL-BHB) (FIG. 3).

Example 3: Protection Against Mortality Caused by 3-Nitropropionic Acid by Uridine and Sodium Beta-Hydroxybutyrate Alone and in Combination Uridine and beta-hydroxybutyrate both display protective effects against toxicity and mortality caused by 3-nitropropionic acid (3-NP), an inhibitor of Complex II of the mitochondrial respiratory chain that is used to model disorders of the brain and other tissues that involve failure of mitochondrial energy production.

Subcutaneous administration of therapeutic agents is a suitable route of administration for emergency drugs that are intended to be used in people with traumatic brain injury, stroke or asphyxia, where the patient may not be capable of ingesting oral medications or may be in a situation where it is difficult to place an intravenous catheter. Subcutaneous drug administration is practical, but the composition must conform to volumes and osmolality values that are known to be compatible with this route of administration; excessively high osmolality can cause local edema, and volumes must be low enough for injection without problematic back pressure. Compositions comprising uridine, sodium beta-hydroxybutyrate and a combination of the two, with the osmolality restricted to a maximum of 800 milliosmoles/liter (a value known to be acceptable for subcutaneous fluid administration) were tested in a model of whole-body energy failure induced by daily intraperitoneal injections of 3-nitropropionic acid at two dose levels, 65 mg/kg/day and 70 mg/kg/day.

Survival times (median survival; the time point at which 50% of animals in a group had died) and percent survival at the end of a 13 day study were used to quantify and compare protective effects of the test agents.

Female CD-1 mice at approximately 16 weeks of age were divided into weight-matched groups of 10 mice each. All mice received daily intraperitoneal injections of 3-NP (65 mg/kg or 70 mg/kg) in a volume of 0.01 ml per gram of body weight at 5 PM.

The therapeutic treatments were administered by subcutaneous injection in a volume of 0.02 ml/gram of body weight three times per day, at 7 AM and 12 PM and 4 PM. 3-NP was administered at 5 PM on each of the consecutive days of the experiment. Body weights were recorded each day to adjust drug doses as mice lost weight during repeated treatment with 3-NP. D-BHB was administered as the water soluble sodium salt Na(D-BHB) (Toronto Research Chemicals, catalog #H833025.

Groups:

1. Vehicle Control—0.9% saline t.i.d.
2. Uridine 200 mg/kg t.i.d.
3. Na(D-BHB) 985 mg/kg t.i.d.
4. Uridine 200 mg/kg+Na(D-BHB) 985 mg/kg t.i.d.

Figure 4:
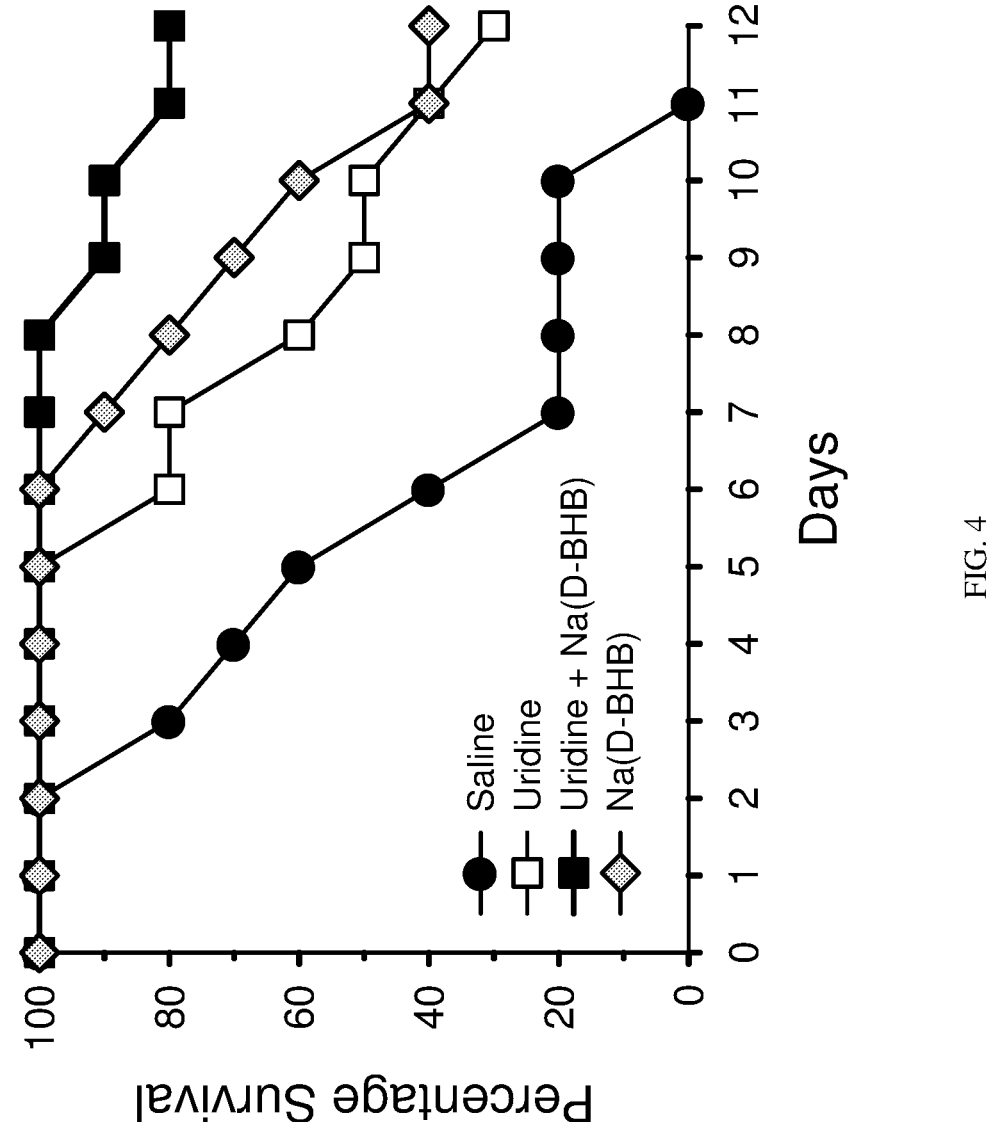
FIG. 4: Survival of mice receiving 65 mg/kg/day 3-nitropropionic acid and treated with subcutaneous uridine 200 mg/kg t.i.d. and Na(D-BHB) 985 mg/kg t.i.d. alone and in combination
Figure 5:
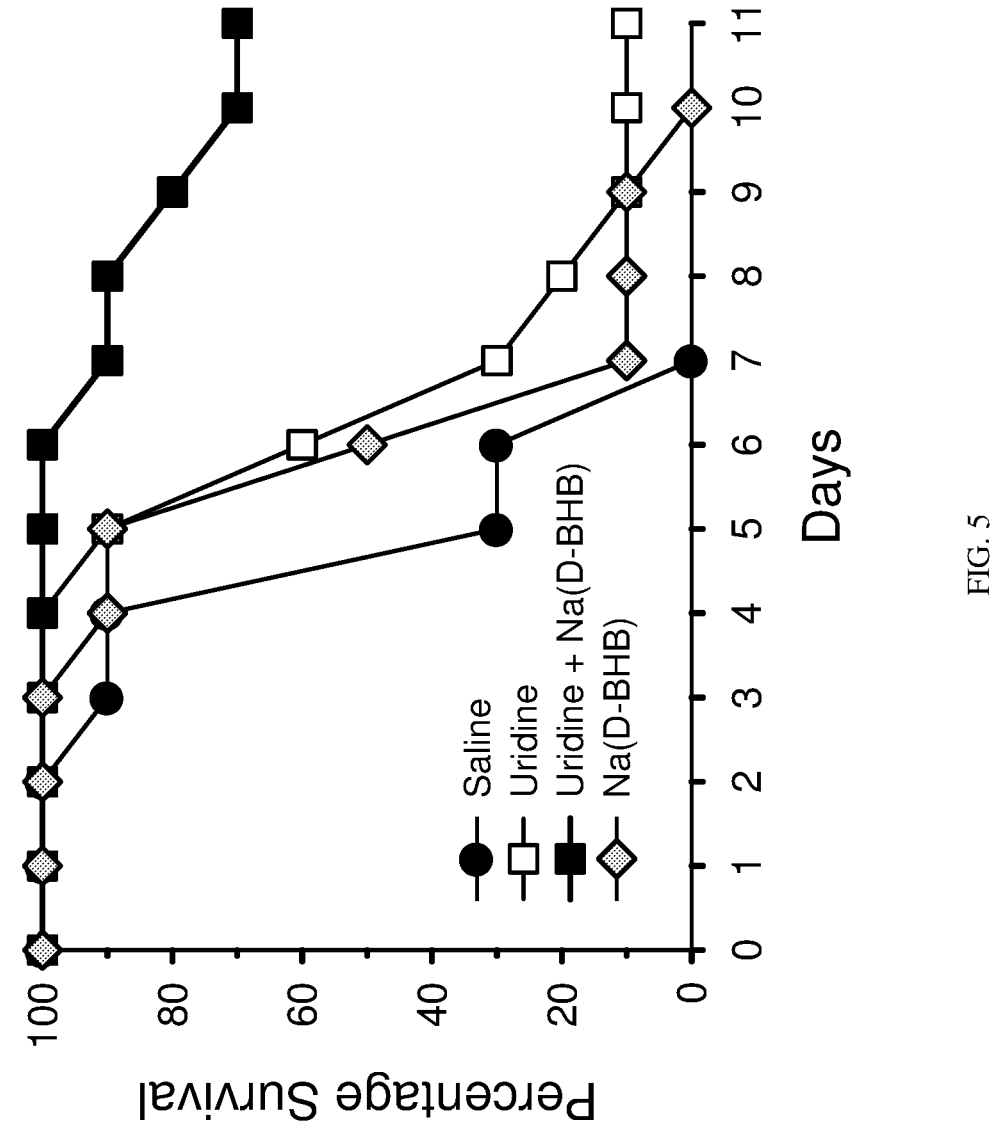
FIG. 5: Survival of mice receiving 70 mg/kg/day 3-nitropropionic acid and treated with subcutaneous uridine 200 mg/kg t.i.d. and Na(D-BHB) 985 mg/kg t.i.d. alone and in combination

Results:

Mice in the Vehicle Control group began to die on Day 4 after initiation of 3-NP dosing. The final survival percentages and median survival times at the end of the studies are shown in the following tables and in FIGS. 4 and 5.

TABLE 3

Survival of mice receiving with 65 mg/kg/day 3-nitropropionic acid and treated with subcutaneous uridine 200 mg/kg t.i.d. and Na(D-BHB) 985 mg/kg t.i.d. alone and in combination

| Group | % Survival | Median Survival |
|---|---|---|
| Vehicle Control | 0% (0/10) | 5.5 Days |
| Uridine | 30% (3/10) | 9 Days |
| Na(D-BHB) | 40% (4/10) | 10.5 Days |
| Uridine + Na(D-BHB) | 80% (8/10) | >12 Days |

TABLE 4

Survival of mice receiving with 70 mg/kg/day 3-nitropropionic acid and treated with subcutaneous uridine 200 mg/kg t.i.d. and Na(D-BHB) 985 mg/kg t.i.d. alone and in combination

| Group | % Survival | Median Survival |
|---|---|---|
| Vehicle Control | 0% (0/10) | 4.5 Days |
| Uridine | 10% (1/10) | 6.5 Days |
| Na(D-BHB) | 0% (0/10) | 6 Days |
| Uridine + Na(D-BHB) | 70% (7/10) | >11 Days |

These results indicate that the subcutaneous administration of uridine alone provided substantial protection against the lethal toxicity of repeat-dose 3-NP. NaBHB in the dose used in this study provided protection similar to that of uridine. The combination of uridine and NaBHB was superior to either uridine or NaBHB alone, with a markedly larger advantage (greater than additive) for the combination at the higher dose of 3-nitropropionic acid (70 mg/kg/day).

Example 4: Pharmacokinetics of Plasma Uridine
and Na(D-BHB) after Subcutaneous Administration Subcutaneous injections of a combination of uridine and Na(D-BHB) (sodium salt of the D isomer of beta-hydroxybutyrate) provides protection against morbidity and mortality due to impaired mitochondrial energy production in mouse models. Translation of this protective effect to larger animals including humans depends on the ability to attain protective concentrations of uridine and BHB in plasma with a practical dose and volume for subcutaneous injection.

There is a ceiling on osmolality of solutions for subcutaneous administration due to the possibility of local osmotic edema if the concentration of solutes is too high. Approximately 800 milliosmoles/liter is considered an upper limit for concentration of therapeutic subcutaneous fluids. In studies conducted on mice receiving daily doses of the mitochondrial Complex II inhibitor 3-nitropropionic acid, a subcutaneous composition comprising uridine and the sodium salt of D-BHB, with total solute concentrations capped at <800 milliosmolar, was found to confer marked protection against mortality caused by mitochondrial failure. Three daily doses were found to provide superior protection. A pharmacokinetic study was conducted to determine plasma concentrations of uridine and D-BHB attained after administration of therapeutic doses of the composition, to determine concentrations and durations of exposure that must be attained for translation of the protective effect to other species including humans.

Groups of 8 mice (Female CD-1 mice, approximately 16 weeks old) were treated with subcutaneous uridine or uridine plus Na(D-BHB) as indicated in the table below. D-BHB was administered as the water soluble sodium salt Na(D-BHB) (Toronto Research Chemicals, catalog #H833025

| Group No. | Group ID | Uridine (mg/Kg) | NaBHB (mg/Kg) |
| --- | --- | --- | --- |
| 1 | 200Uri + Na(D-BHB) | 200 | 985.1 |
| 2 | 300Uri + Na(D-BHB) | 300 | 985.1 |
| 3 | 400Uri + Na(D-BHB) | 400 | 985.1 |
| 4 | 400Uri | 400 | — |

1. Group 1 (200 mg/kg Uridine+Na(D-BHB) received 10 mg/ml uridine and 49.26 mg/ml Na(D-BHB) (0.02 ml/g bw).
2. Group 2 (300 mg/kg Uridine+Na(D-BHB) received 15 mg/ml uridine and 49.26 mg/ml Na(D-BHB) (0.02 ml/g bw).
3. Group 3 (400 mg/kg Uridine+Na(D-BHB) received 20 mg/ml uridine and 49.26 mg/ml Na(D-BHB) (0.02 ml/g bw).
4. Group 4 (400 mg/kg Uridine) received 20 mg/ml uridine (0.02 ml/g bw).

Blood samples were obtained from the retro-orbital plexus at time points of 15, 30, 60 and 120 minutes after drug injection. Two blood samples (<200 microliters) were collected from each mouse into heparinized polyethylene tubes, with 4 mice bled at 15 and 60 minutes, and the other 4 mice in a group were bled at 30 and 120 minutes. Plasma samples were obtained by centrifugation, and were deproteinized and analyzed for uridine and uracil by an LC/MS method. Plasma D-BHB was measured in the same samples by a commercial enzymatic color-change assay.

Rodents degrade uridine to uracil more rapidly and extensively than do humans, who have lower activities of the enzyme uridine phosphorylase. Therefore, it is important to take into account plasma uracil concentrations in rodents for optimum translation of rodent pharmacokinetic results to the human situation. The sum of uridine+uracil in rodents is a better reflection of plasma uridine equivalents than is uridine alone for translation to other animal models or to human dosing.

Figure 6:
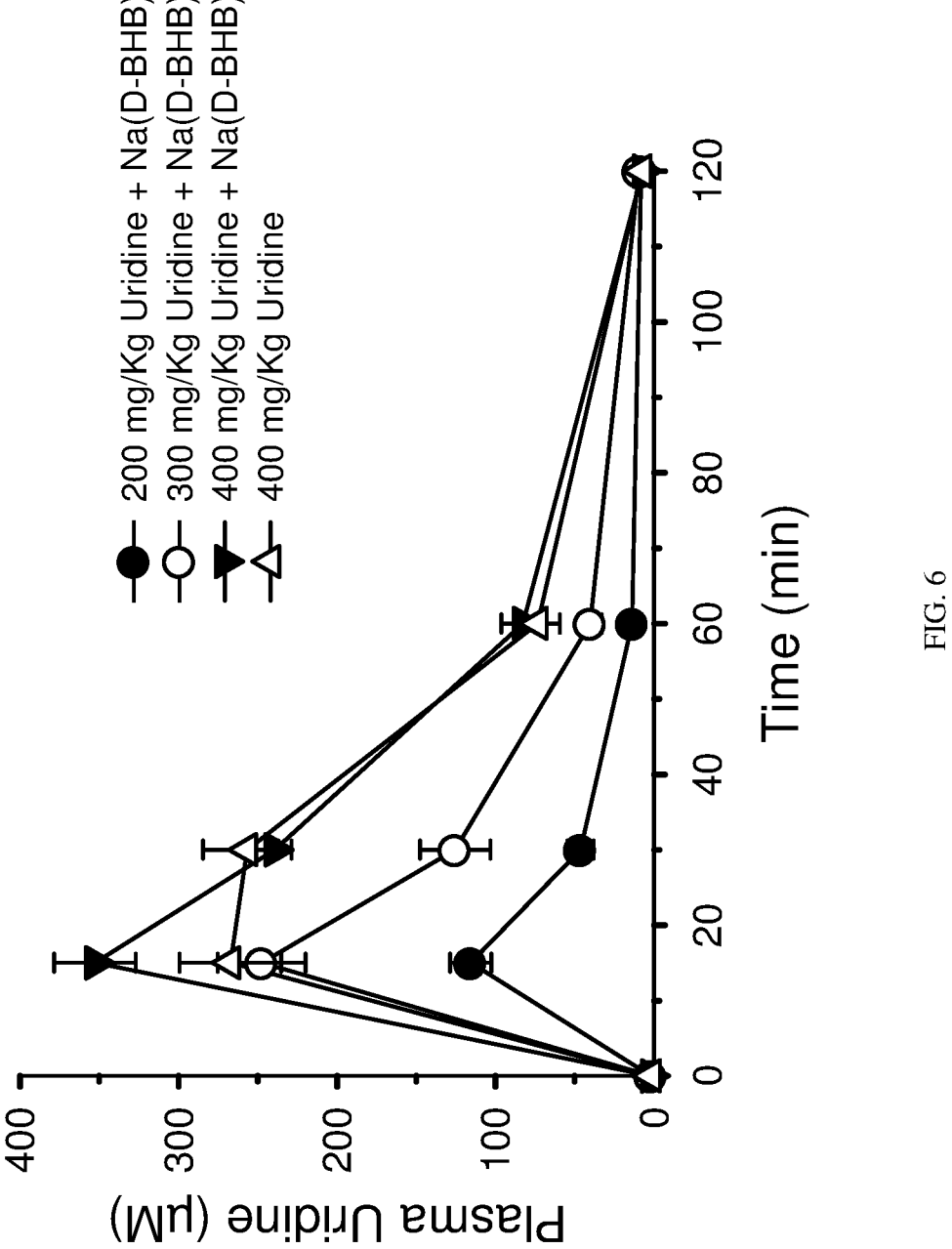
FIG. 6: Plasma uridine after subcutaneous administration of uridine or uridine+Na(D-BHB)
Figure 7:
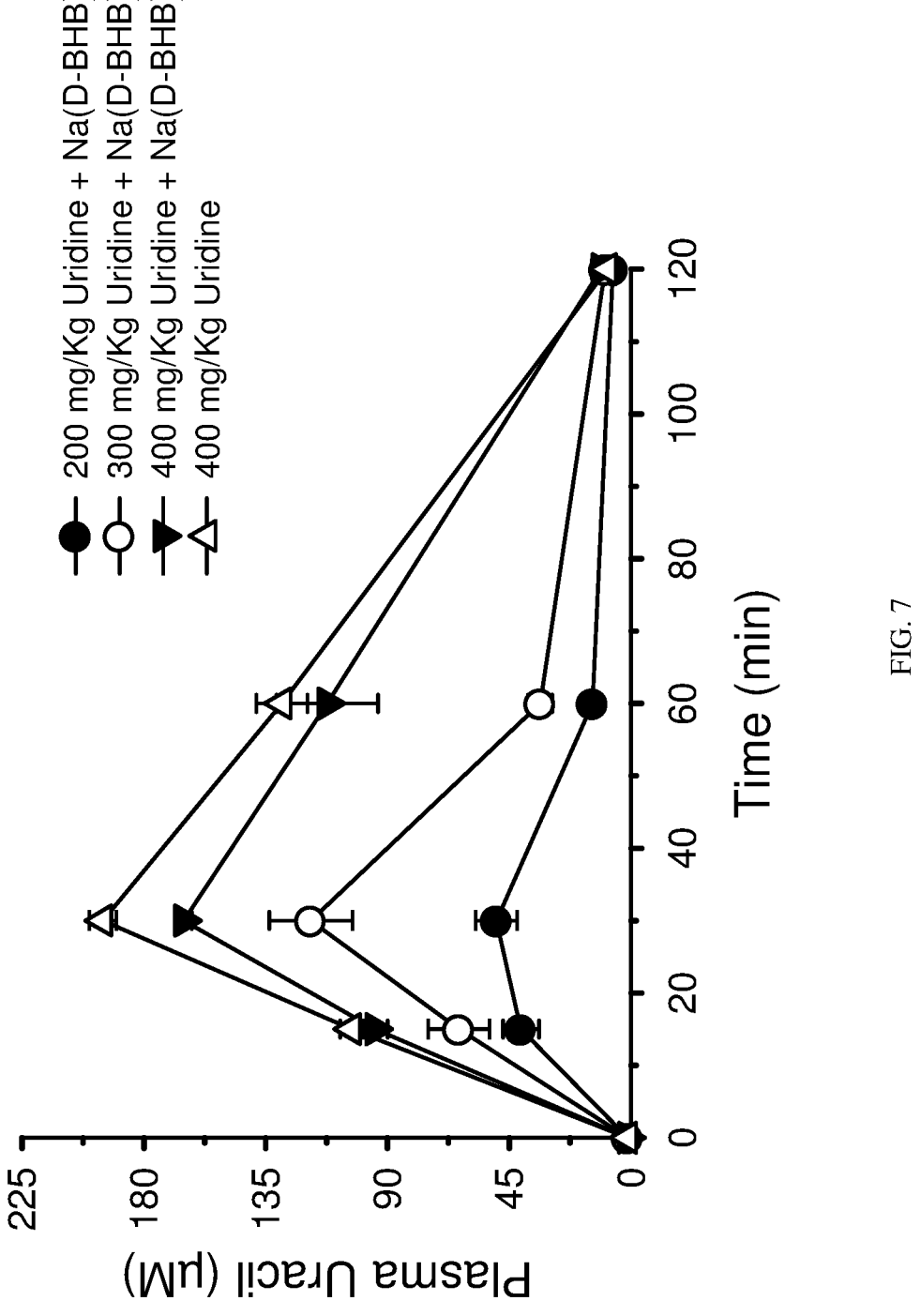
FIG. 7: Plasma uracil after subcutaneous administration of uridine or uridine+Na(D-BHB)
Figure 8:
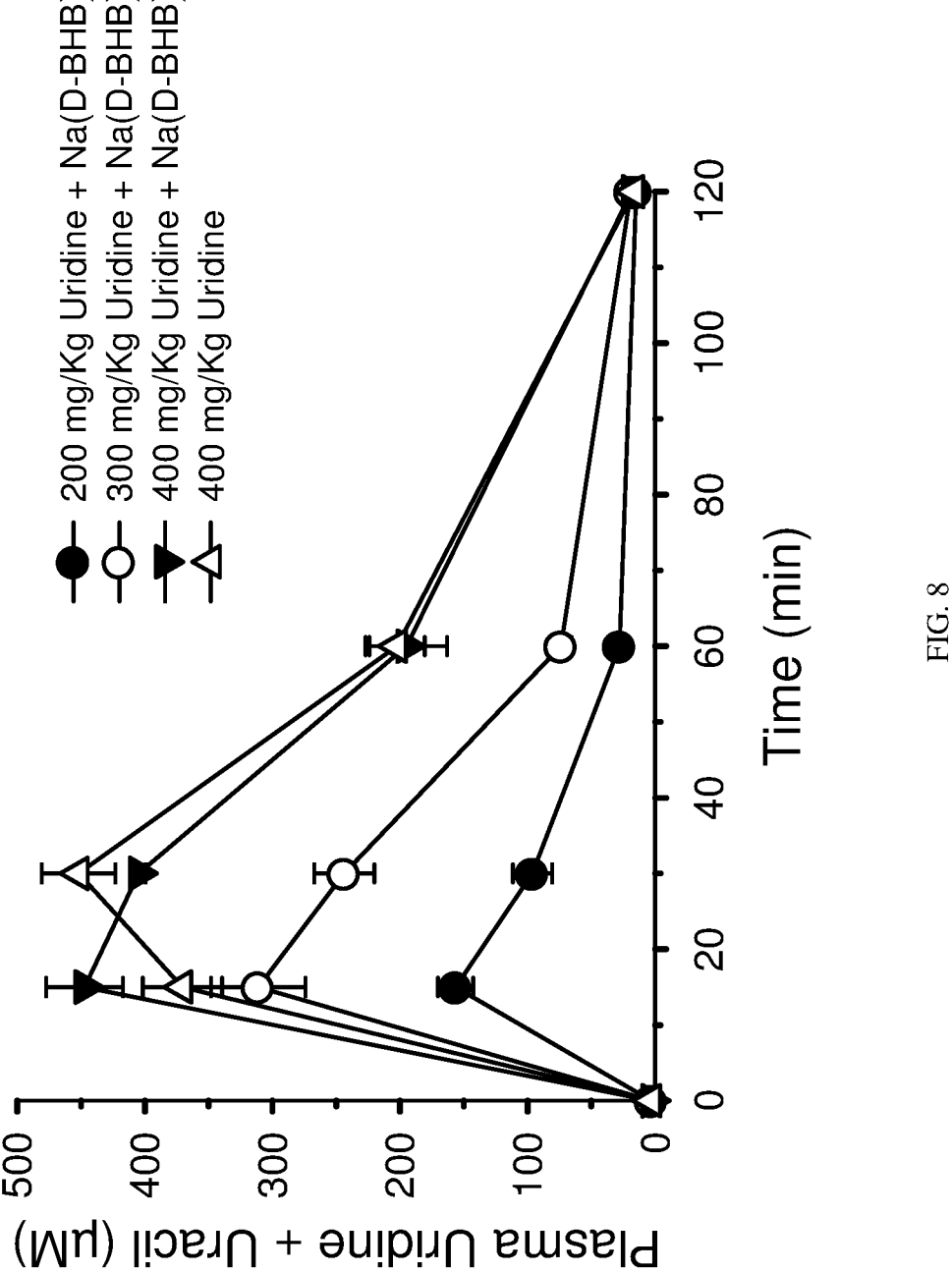
FIG. 8: Plasma [uridine+uracil] after subcutaneous administration of uridine or uridine+Na(D-BHB)
Figure 9:
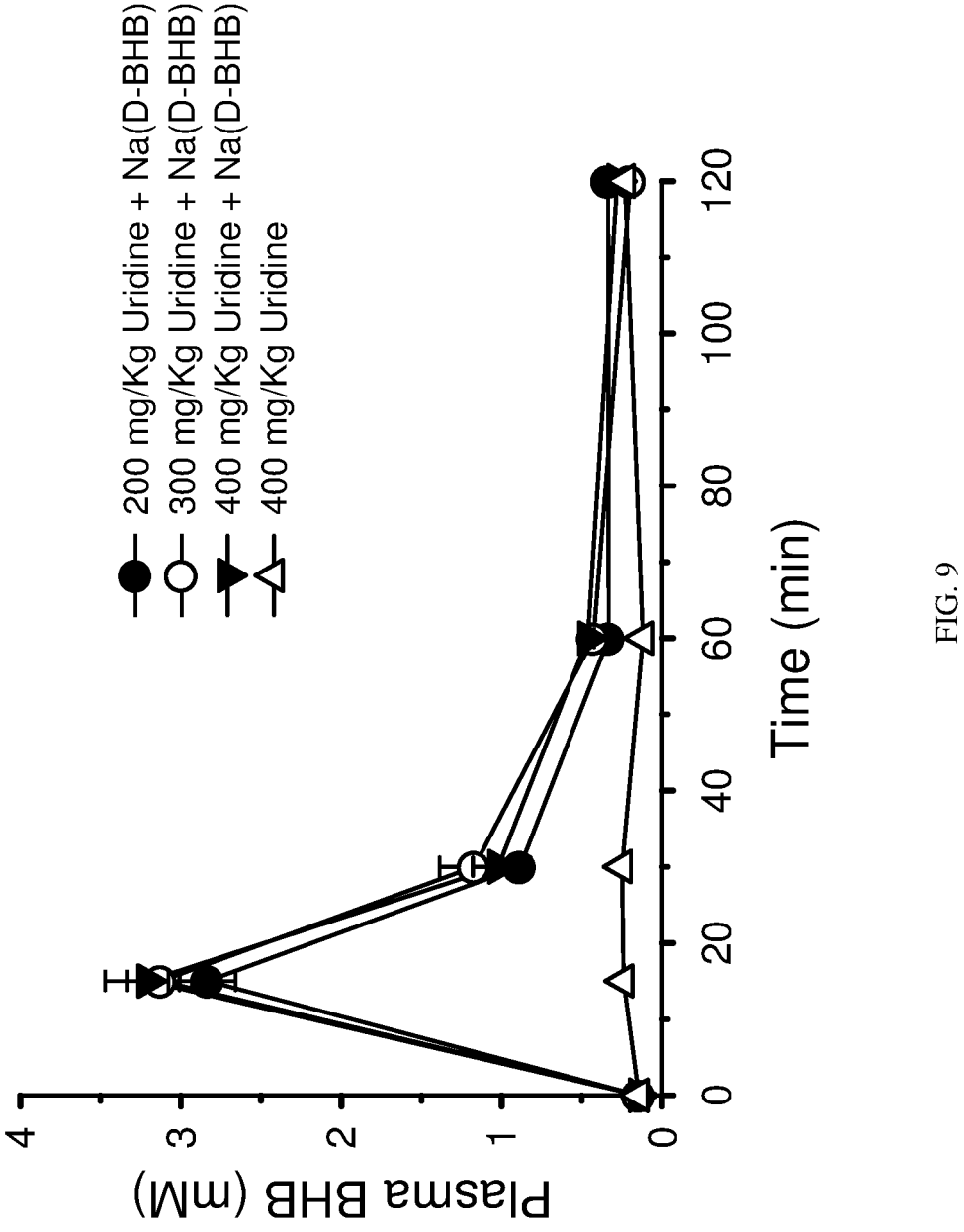
FIG. 9: Plasma D-beta-hydroxybutyrate after subcutaneous administration of uridine or uridine+Na(D-BHB)

Uridine (and uridine+uracil) appeared in plasma rapidly after subcutaneous administration with a Tmax of 15 to 30 minutes after dosing (FIGS. 6, 7 and 8). Plasma D-BHB also rose rapidly, with a Tmax at 15 minutes (FIG. 9). Plasma uridine (and uridine+uracil) displayed dose-dependent C max values (FIGS. 6, 7 and 8).

The uridine+Na(D-BHB) dosing regimen in this pharmacokinetic study had previously been shown to yield strong protective effects against mortality caused by daily injections of 3-nitropropionic acid. The pharmacokinetic data indicate that periodic transient elevation of plasma uridine and BHB is sufficient to induce robust protection against lethal systemic mitochondrial energy failure. The maximum concentrations of plasma uridine+uracil at the highest dose of 400 mg/kg uridine are less than 500 micromolar, which is below the threshold for inducing hyperthermia and shivering in humans, which was a reported clinical problem with intravenous administration of uridine. The maximum D-BHB concentration observed in this study, approximately 3 millimolar, is known to be well-tolerated in humans, equivalent to concentrations observed during post-exercise ketosis, and well below thresholds for ketoacidosis (>15 mM).

What is claimed is:

1. A pharmaceutical composition comprising a neuroprotective amount of uridine, a neuroprotective amount of the D-enantiomer of beta-hydroxybutyrate (D-BHB), and a cationic counterion,
    wherein the uridine, the D-BHB, and the cationic counterion are dissolved in saline solution, and
    wherein the pharmaceutical composition is formulated for subcutaneous injection to a human subject, and the amount of the uridine is from 10 to 40 mg/kg by weight of the human subject; and the amount of the D-BHB is from 50 to 100 mg/kg by weight of the human subject.

2. The pharmaceutical composition of claim 1, wherein the cationic counterion is selected from the group consisting of $Na^+$, $Mg^{2+}$, and both.

3. The pharmaceutical composition of claim 1, wherein the saline solution further comprises an organic anion selected from the group consisting of an amino acid, gluconate, pyroglutamate, citrate, acetate, and lactate.

4. The pharmaceutical composition of claim 3, wherein the amino acid is threonine or aspartate.

5. The pharmaceutical composition of claim 1, wherein the solution further comprises a hypothermic agent.

6. The pharmaceutical composition of claim 1, wherein the saline solution is isotonic or hypertonic saline.

7. The pharmaceutical composition of claim 1, wherein the amount of uridine is sufficient to maintain plasma uridine at a concentration from 200 to 500 micromolar for about one hour in the human subject.

8. The pharmaceutical composition of claim 1, wherein the human subject is a human adult, wherein the cationic counterion comprises $Mg^{2+}$ in an amount of from 10 to 40 milliEquivalents.

9. The pharmaceutical composition of claim 1, wherein the human subject is a human child, and wherein the cationic counterion comprises $Mg^{2+}$ in an amount of from 5 to 10 milliEquivalents.

10. The pharmaceutical composition of claim 1, wherein the cationic counterion comprises Na$^+$.

11. The pharmaceutical composition of claim 1, wherein the cationic counterion comprises Mg$^{2+}$.

12. The pharmaceutical composition of claim 1, wherein the cationic counterion comprises both, Na$^+$ and Mg$^{2+}$.

\* \* \* \* \*